(12) United States Patent
Hsiung et al.

(10) Patent No.: US 9,884,320 B2
(45) Date of Patent: Feb. 6, 2018

(54) SYSTEM AND METHOD FOR DETECTING BIOMARKER

(71) Applicant: Winnoz Technology, Inc., Taipei (TW)

(72) Inventors: Le-Chang Hsiung, Taipei (TW); Po-Yang Wang, Taipei (TW); Po-Chun Chen, Taipei (TW); Chuan Whatt Eric Ou, Singapore (SG)

(73) Assignee: Winnoz Technology, Inc., Taipei (TW)

( * ) Notice: Subject to any disclaimer, the term of this patent is extended or adjusted under 35 U.S.C. 154(b) by 0 days.

(21) Appl. No.: 15/141,987

(22) Filed: Apr. 29, 2016

(65) Prior Publication Data

US 2016/0318018 A1    Nov. 3, 2016

Related U.S. Application Data

(60) Provisional application No. 62/155,150, filed on Apr. 30, 2015.

(51) Int. Cl.
*B01L 3/00* (2006.01)
*G01N 33/68* (2006.01)
*G01N 33/72* (2006.01)
*C12Q 1/68* (2006.01)

(52) U.S. Cl.
CPC .... *B01L 3/502753* (2013.01); *G01N 33/6803* (2013.01); *G01N 33/721* (2013.01); *B01L 2200/10* (2013.01); *B01L 2300/06* (2013.01); *B01L 2300/069* (2013.01); *B01L 2300/0636* (2013.01); *B01L 2300/0681* (2013.01); *B01L 2300/087* (2013.01); *B01L 2300/0883* (2013.01); *B01L 2400/043* (2013.01);

(Continued)

(58) Field of Classification Search
CPC .. C12M 1/00; C12M 1/34; C12Q 1/68; G01N 31/22; B01L 3/5027
See application file for complete search history.

(56) References Cited

U.S. PATENT DOCUMENTS

2004/0018611 A1* 1/2004 Ward ............... B82Y 15/00
435/287.2
2007/0122819 A1* 5/2007 Wu ............... B01L 3/502746
435/287.2

(Continued)

FOREIGN PATENT DOCUMENTS

| CN | 1786710 | 6/2006 |
|---|---|---|
| CN | 101142314 | 3/2008 |
| CN | 101305279 | 11/2008 |

(Continued)

OTHER PUBLICATIONS

Quian et al, Magneto-hydrodynamics based microfluidics, Mechanics Research Communications, 2009, 36, 10-21.*

(Continued)

*Primary Examiner* — Narayan Bhat
(74) *Attorney, Agent, or Firm* — Amin, Turocy & Watson, LLP

(57) ABSTRACT

A system for detecting one or more biomarkers is provided, the system comprising: an inlet region for receiving a sample; a channel connected with the inlet region, wherein the channel allows the sample to move along thereof; multiple functional zones arranged along the channel in a designated distribution; and a driving mechanism to force the sample to move along the channel.

28 Claims, 15 Drawing Sheets

(52) U.S. Cl.
CPC . *B01L 2400/0406* (2013.01); *B01L 2400/088* (2013.01); *C12Q 1/6806* (2013.01)

(56) References Cited

U.S. PATENT DOCUMENTS

2010/0203521 A1    8/2010  Klapperich et al.
2012/0070833 A1*   3/2012  Wang ................ B01L 3/502776
                                                          435/6.11

FOREIGN PATENT DOCUMENTS

CN        101379387        3/2009
WO        2010/009415 A1   1/2010

OTHER PUBLICATIONS

International Search Report for International Patent Application No. PCT/CN2016/080693 dated Jul. 18, 2016, 4 pages.
Written Opinion for International Patent Application No. PCT/CN2016/080693 dated Jul. 18, 2016, 4 pages.

* cited by examiner

SYSTEM AND METHOD FOR DETECTING BIOMARKER

BACKGROUND OF THE DISCLOSURE

1. Field of the Disclosure

The present disclosure relates to a system for detecting biomarkers and a method thereof, particularly a microfluidic system for processing a biosample for the detection of a biomarker, and a method thereof.

2. Description of the Related Art

Conventionally, an ordinary blood test for detecting biomarkers (e.g., exosome, protein, miRNA, hemoglobin, and small molecules) involves complicated procedures to process a raw biosample, such as a whole blood sample. Since the preliminary procedures (e.g. centrifugation, lysis, concentration, and dilution) for processing a biosample are generally not available using a conventional microfluidic chip, additional procedures have to be performed in a laboratory prior to injecting the biosample into the microfluidic system. However, such additional procedures incur additional cost and time, which may also limit the types of detectable biomarkers. For example, some biomarkers, such as intracellular components, can be detected only if the cells are broken down by preliminary processes, such as lysis, to release target biomarkers.

As shown in FIG. 1, a conventional microfluidic chip including a processing zone 11, a mixing zone 12, a detection zone 16 and an absorbent zone 6 is usually designed for the detection of a single biomarker of a biosample 3. In order to detect multiple biomarkers using a microfluidic chip, different kits corresponding to different biomarkers for processing a biosample are required. Besides, some common processing procedures, such as filtering, have to be performed repeatedly in different kits, which result in an unnecessary waste and cause a crucial problem of using a scarce sample.

To overcome the technical problems mentioned above, there is a need to provide a new microfluidic system to simplify operating procedures and to reduce unnecessary waste.

SUMMARY OF THE DISCLOSURE

The present disclosure provides a system for detecting one or multiple biomarkers, comprising: an inlet region for receiving a sample; a channel connected with the inlet region, wherein the channel allows the sample to move along thereof; multiple functional zones arranged along the channel in a designated distribution; and a driving mechanism to force the sample to move along the channel.

According to another aspect of the present disclosure, the present disclosure provides a method of detecting one or multiple biomarkers, comprising: providing an inlet region for receiving a sample; providing a channel for allowing the sample to move along thereof; arranging multiple functional zones along the channel in a designated distribution; and providing a driving mechanism to force the sample to move along the channel.

These and other features and advantages of the system and method of the disclosure are described below with respect to illustrative embodiments of the disclosure.

Figure 1:
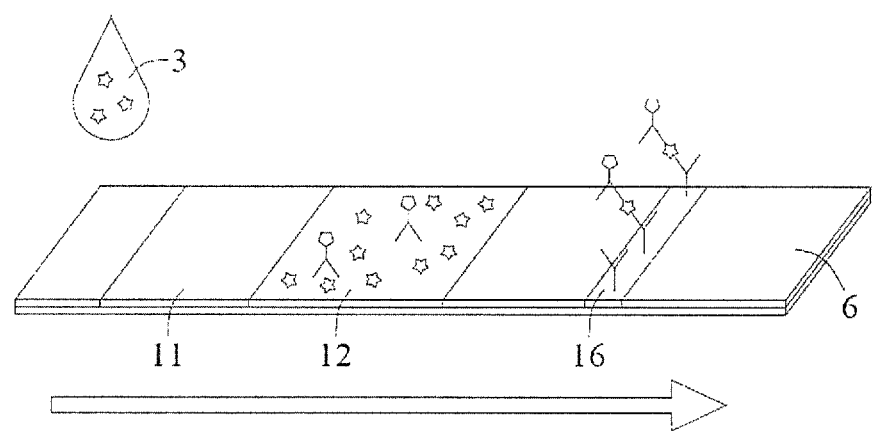
FIG. 1 shows a schematic view of a channel of a conventional microfluidic chip.

| Reference Sign List | |
| --- | --- |
| 3 | Biosample |
| 5 | Biomarker |
| 6 | Absorbent zone |
| 7 | Magnet |
| 9 | Magnetic particle |
| 11 | Processing zone |
| 12 | Mixing zone |
| 16 | Detection zone |
| 100 | System |
| 101 | Inlet region |
| 102 | Channel |
| 111 | Filtration/separation zone |
| 112 | Mixing/reaction zone |
| 113 | Lysis zone |
| 114 | Dilution zone |
| 115 | Concentration zone |
| 116 | Detection zone |
| 117 | Absorbent zone |
| 201 | Inlet region |
| 203 | Channel |
| 205 | Channel |

-continued

Reference Sign List

| | |
|---|---|
| 207 | Channel |
| 211 | Filtration/separation zone |
| 216 | Detection zone |
| 221 | Filtration/separation zone |
| 231 | Filtration/separation zone |
| 241 | Filtration/separation zone |
| 312 | Mixing zone |
| 322 | Reaction zone |
| 413 | Lysis zone |
| 423 | Lysis zone |
| 433 | Lysis zone |
| 514 | Dilution zone |
| 524 | Dilution zone |
| 615 | Concentration zone |
| 625 | Concentration zone |
| 635 | Concentration zone |
| 636 | Detection zone |
| 645 | Concentration zone |
| 646 | Detection zone |
| 712 | Mixing/reaction zone |
| 716 | Detection zone |
| 726 | Detection zone |
| 735 | Concentration zone |
| 736 | Detection zone |
| 745 | Concentration zone |
| 746 | Detection zone |
| 800 | System |
| 801 | Inlet region |
| 811 | Filtration/separation zone |
| 812 | Mixing/reaction zone |
| 815 | Concentration zone |
| 816 | Detection zone |
| 817 | Absorbent zone |
| 821 | Filtration/separation zone |
| 822 | Mixing/reaction zone |
| 825 | Concentration zone |
| 826 | Detection zone |
| 831 | Filtration/separation zone |
| 832 | Mixing/reaction zone |
| 835 | Concentration zone |
| 836 | Detection zone |
| 841 | Filtration/separation zone |
| 846 | Detection zone |
| 900 | System |
| 901 | Inlet region |
| 911 | Filtration/separation zone |
| 912 | Mixing/reaction zone |
| 913 | Lysis zone |
| 915 | Concentration zone |
| 916 | Detection zone |
| 917 | Absorbent zone |
| 921 | Filtration/separation zone |
| 926 | Detection zone |
| 1000 | System |
| 1001 | Inlet region |
| 1011 | Filtration/separation zone |
| 1012 | Mixing/reaction zone |
| 1015 | Concentration zone |
| 1016 | Detection zone |
| 1017 | Absorbent zone |
| 1022 | Mixing/reaction zone |
| 1025 | Concentration zone |
| 1026 | Detection zone |
| 1100 | system |
| 1101 | Inlet region |
| 1111 | Filtration/separation zone |
| 1112 | Mixing/reaction zone |
| 1113 | Lysis zone |
| 1115 | Concentration zone |
| 1116 | Detection zone |
| 1117 | Absorbent zone |

DETAILED DESCRIPTION OF THE DISCLOSURE

The following specific embodiments are provided to illustrate the present disclosure, the advantages and effects can be apparently understood by those skilled in the art after reading the disclosure of this specification.

It should be understood, the accompanying drawings depicted structure, proportion, size, etc., are disclosed only to illustrate the content of the specification, to facilitate the understanding and reading of those skilled in the art, but not intend to limit the present disclosure in specific conditions, and do not have technical substantial meaning. Any modification of the structure, change of the ratio relation, or adjustment of the size should be involved in the scope of disclosures in this specification without influencing the producible efficacy and the achievable objective of this specification. Those changes or adjustments of relative relationship without substantial change of technical content should also be considered within the category of implementation.

Figure 2:
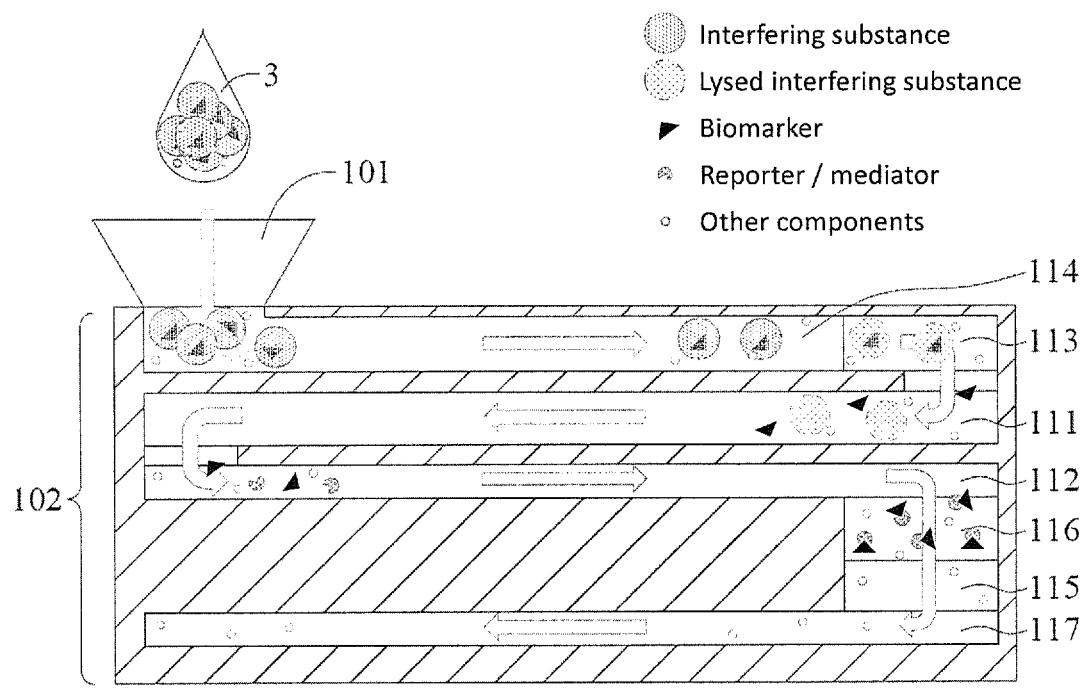
FIG. 2 shows a cross-sectional view of a microfluidic system according to an embodiment of the present disclosure.

FIG. 2 illustrates an exemplary schematic view of a system 100 for detecting one or multiple biomarkers according to an embodiment of the present disclosure. The system 100 includes: an inlet region 101 for receiving a sample, a channel 102 connected with the inlet region 101 allowing the sample to move along the channel 102, and multiple functional zones arranged along the channel in a designated distribution. In an embodiment, the multiple functional zones may include, for example, a filtration/separation zone 111, a mixing/reaction zone 112, a lysis zone 113, a dilution zone 114, a concentration zone 115, a detection zone 116, and an absorbent zone (sink) 117. In the system 100, a driving mechanism, such as surface tension, capillarity action, or other applicable driving mechanisms, is provided to force the sample to move along the channel 102 toward an absorbent zone 117.

In an embodiment shown in FIG. 2, the inlet region 101 is provided for receiving a sample which may include, for example but not limited to, a biosample 3, such as blood, urine, or saliva.

Figure 3A:
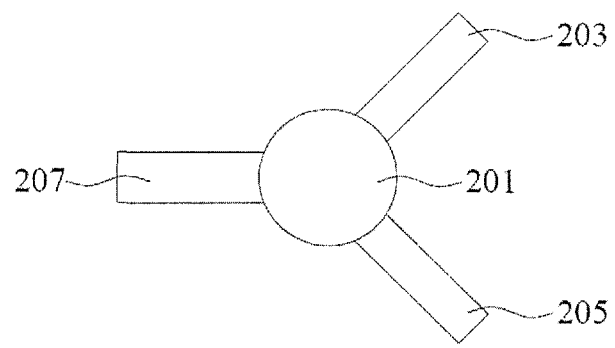
FIG. 3(A) shows a top view of an inlet of a microfluidic system according to an embodiment of the present disclosure.

In an embodiment, the inlet region can branch out into more than one channel. As shown in FIG. 3(A), the inlet region 201 can branch out into three different channels 203, 205 and 207, for example, for extracellular component detection, cell counting and intracellular component detection, respectively.

Figure 3B:
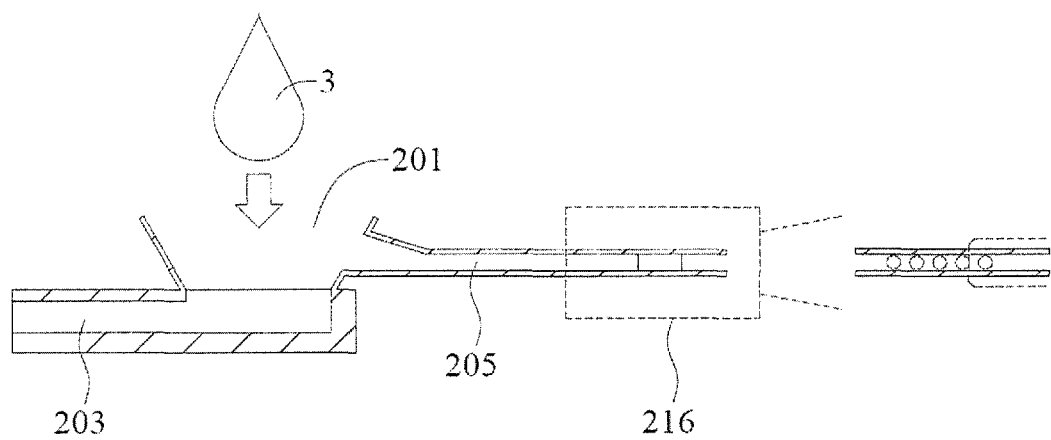
FIG. 3(B) shows a cross-sectional view of an inlet of a microfluidic system according to an embodiment of the present disclosure.

In an embodiment shown in FIG. 3(B), capillary is use as a channel 205 to draw the biosample 3 for cell counting, and the cells are counted based on an applicable mechanism, such as an optical, electrical, or magnetic sensing mechanism.

An embodiment in FIG. 2, the channel 102 can be designed to incorporate desired features according to practical needs. The channel comprises discrete compartments (designated regions of the channel), wherein each compartment contains at least one functional zone. The channel can be a winding path with bending corners.

In an embodiment, the flow rate of the biosample in the channel can be adjusted to allow sufficient reaction time for different reactions in different functional zones. The flow rate of the biosample in the channel can be controlled in different manners as described in the following:

1. Cross-Sectional Area

By controlling dimensions of the channel, the flow rate of a biosample can be correspondingly adjusted. For example, the channel dimensions can be increased to obtain a lower flow rate of the biosample.

2. Material of Channel

The hydrophilicity and hydrophobicity of the channel can also control the flow rate of a biosample. For example, a hydrophilic channel treated with oxygen plasma can be used to accelerate the flow rate of the biosample in the channel. In another embodiment, a hydrophobic channel treated with waxing process can be used to decelerate the biosample in the channel. In another embodiment, the channel can be treated by surfactants to adjust the flow rate of the biosample in the channel.

Moreover, the flow rate can also be adjusted by using different materials. For example, the materials, such as regenerated cellulose, cellulose acetate, cellulose nitrate, polycarbonate, and anodisc, can be arranged at any appropriate position in the channel to adjust the flow rate of a biosample in the channel.

3. Magnetohydrodynamics (MED)

A MED-based flow control can be arranged at any appropriate position in the channel of the system to accelerate or decelerate biomarkers in a biosample. In an embodiment, according to surface charges of biomarkers, an electromagnetic force on biomarkers can be induced by an applied magnetic field via the MHD-based flow control for accelerating or decelerating the biomarkers.

In an embodiment shown in FIG. 2, the functional zones comprise at least one selected from the group consisting of a filtration/separation zone, a mixing/reaction zone, a lysis zone, a dilution zone, a concentration zone, a detection zone, an absorbent zone, and a combination thereof. Persons skilled in the art should appreciate that the functional zones can be designed in various manners, and the same zone can be repeatedly utilized according to practical needs. Furthermore, the functional zones may be arranged in a designated distribution for detecting at least one kind of biomarker. For example, the designated distribution is arranged based on the condition comprising at least one selected from the group consisting of the location of a biomarker, the size of a biomarker, the concentration of a biomarker, the biometric of a biomarker, and a combination thereof.

In the following, the mechanisms of the functional zones are described in details.

a. Filtration/Separation Zone:

The filtration/separation zone is designed for trapping interfering substances in a biosample to reduce signal interference in a detection zone, such that sensitivity and specificity can be improved.

Figure 4A:
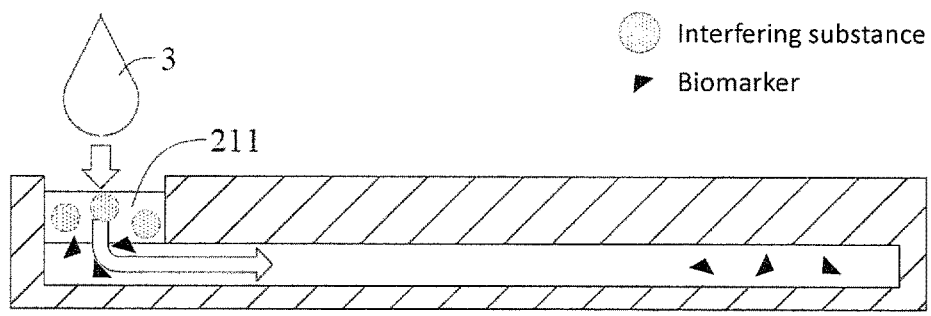
FIGS. 4(A)-(D) are cross-sectional views of filtration/separation zones in different embodiments of the present disclosure.

FIG. 4(A) shows an example of a vertical filtration/separation zone 211 of the present disclosure, in which a filter having specific porosity or pore sizes is provided to retain cells in a biosample 3 and allow the fluid of the biosample 3, such as blood plasma or serum, to flow through the channel continuously.

Figure 4B:
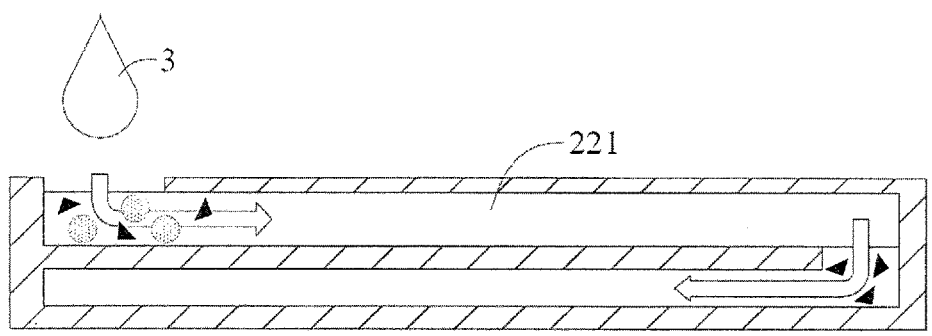
Figure 4C:
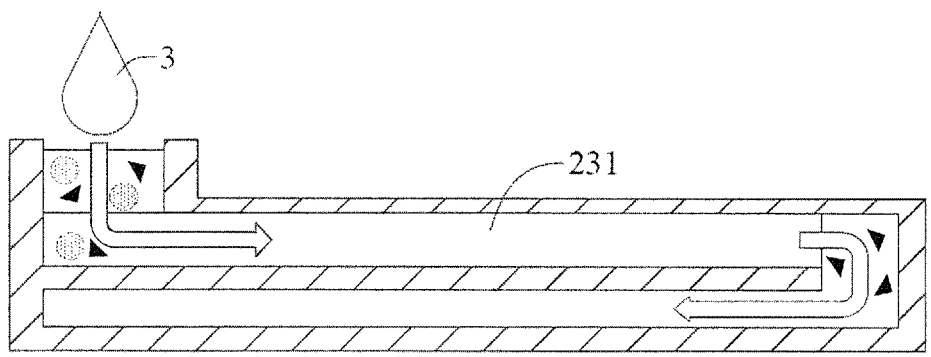

FIG. 4(B) shows another example of a lateral filtration/separation zone of the present disclosure. In an embodiment, a filtration/separation zone 221 is designed as a flow path having micro-channels inside the channel. Specific dimensions of micro-channels depending on the practical needs. By driving a biosample 3 to flow through the zone 221, cells or other interfering substances are trapped, while the desired fluid in the biosample 3, such as blood plasma or serum, keeps flowing through the channel. In addition, it should be noted that the filtration/separation zone 221 can be set in any arrangement for practical needs. For example, the filtration/separation zone 231 can be arranged in a manner as shown in FIG. 4(C), such as the combination of the designs shown in FIG. 4(A) and FIG. 4(B), so as to improve the filtering efficiency in vertical and lateral directions.

Figure 4D:
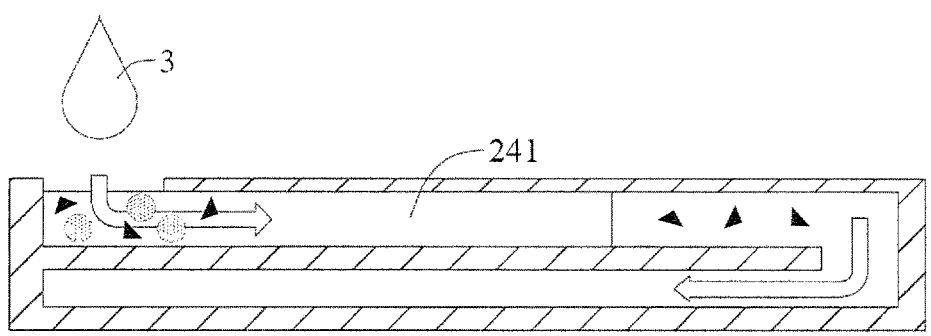

FIG. 4(D) shows another example of a filtration/separation zone 241. The filtration/separation zone 241 can be designed according to electrical properties, specificities, affinities, or other characteristics of biomarkers and other components in a biosample 3.

In another embodiment shown in FIG. 4(D), the filtration/separation zone 241 of the channel can be designed according to electrical properties of target biomarkers and other components in a biosample 3. Regarding blood plasma, components of blood plasma can be categorized into three types according to their electrical properties in a physiological environment, i.e., negatively-charged, positively-charged, and neutral. For example, a positively-charged target biomarker can be separated from negatively-charged interfering substances by using an ionic exchange material to retain the interfering substances in the filtration/separation zone 241. Similarly, negatively-charged target biomarkers can be separated from positively-charged interfering substances.

In another embodiment shown in FIG. 4(D), the filtration/separation zone 241 of the channel can be designed according to specificities and affinities with respect to target components in a biosample. Accordingly, some interfering substances in blood, such as cell, albumin or immunoglobin, can be retained in the filtration/separation zone 241. For example, antibodies against specific interfering substances can be added in the channel, such that the interfering substances will be caught by the antibodies while the biosample flows through the filtration/separation zone.

In another embodiment shown in FIG. 4(D), a nitrocellulose paper can be used as the filtration/separation zone 241 for retaining proteins.

Figure 5A:
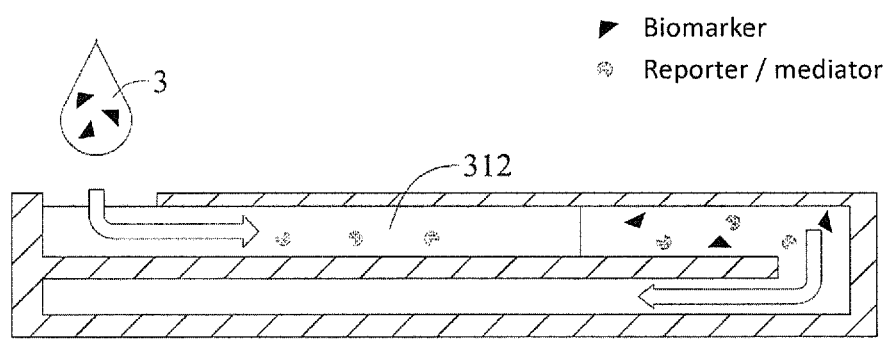
FIGS. 5(A)-(B) are cross-sectional views of mixing/reaction zones in different embodiments of the present disclosure.

Persons skilled in the art should appreciate that the filtration/separation zone can be designed according to any practical needs. It should be also understood, one or more additional filtration/separation zones can be added along the channel.

b. Mixing/Reaction Zone:

Mixing/reaction zone is designed for uniformly and sufficiently mixing biomarkers with reporters or causing reactions between biomarkers and reporters to further improve sensitivity and specificity. In an embodiment shown in FIG. 5(A) and FIG. 5(B), mixing/reaction zones 312, 322 can be prepared as follows. A reporter may be, but not limited to, a mediator, a small molecule, an aptamer, a nucleic acid, an antibody, an enzyme, a protein, a particle, or the likes. The reaction performed in the mixing/reaction zones 312, 322 may be, but not limited to, a protein-protein interaction, an antigen-antibody interaction, a protein-nucleic acid interaction, an enzymatic reaction, a redox reaction, a chemical reaction, or a combination thereof. The mixing/reaction zones 312, 322 can be coated with reporters corresponding to target biomarkers. The appropriate matching of biomarkers and reporters used in the mixing/reaction zone is shown in Table 1 below.

TABLE 1

| Biomarkers | Types of reporters in the mixing/reaction zone |
| --- | --- |
| Exosome | Aptamer, protein, antibody, small molecule, particle |
| Protein | Aptamer, protein, antibody, small molecule, particle |

TABLE 1-continued

| Biomarkers | Types of reporters in the mixing/reaction zone |
|---|---|
| miRNA | Protein, nucleic acid, particle |
| Small molecule | Enzyme, small molecule |

Figure 5B:
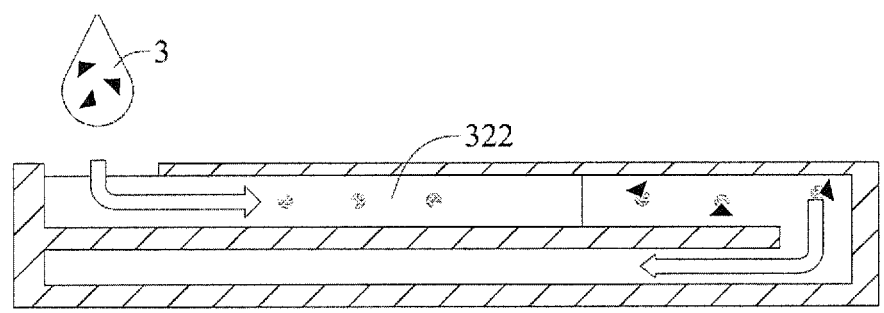
Figure 6A:
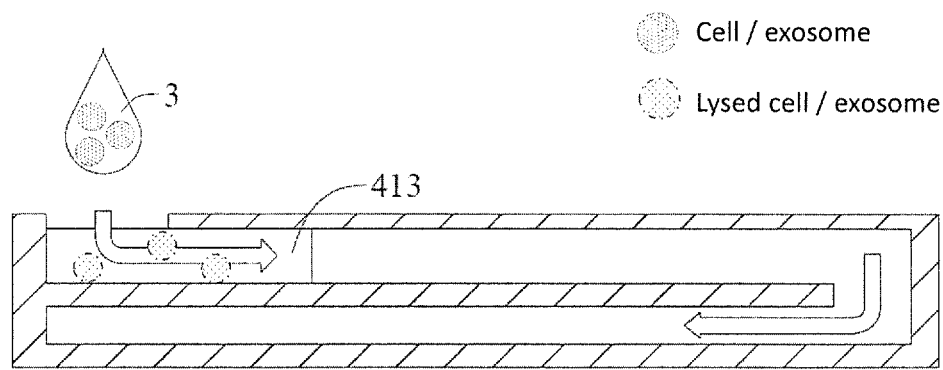
FIGS. 6(A)-(C) are cross-sectional views of lysis zones in different embodiments of the present disclosure.

In another embodiment, biomarkers can form complexes with reporters in a mixing/reaction zone 322 (FIG. 5(B)) prior to entering a filtration/separation zone 241 (FIG. 4(D)). The filtration/separation zone 241 is incorporated with magnetohydrodynamics (MHD)-based flow control. The complexes and the unreacted reporters carry different net surface charges. Therefore, when the complexes and the unreacted reporters flow along the filtration/separation zone 241, they experience an applied magnetic field which is perpendicular to the filtration/separation zone 241. As a result, flow velocity of the complexes and that of the unreacted reporters will be differentiated by different resultant electromagnetic forces.

c. Lysis Zone:

The lysis zone is designed for breaking membranes of cells, exosomes, or other vesicles, such that biomarkers (such as proteins, RNAs, DNAs, or metabolites therein) can be released into the solution for subsequent detections. As shown in FIG. 6(A), a lysing agent for lysing cells, exosomes, or other vesicles is provided in a lysis zone 413, so that cells, exosomes, or other vesicles can be lysed in the lysis zone 413. In an embodiment, a lysis zone 413 is coated with a lysing agent, such as detergent or streptolysin, for lysing cells, exosomes, or other vesicles.

Figure 6B:
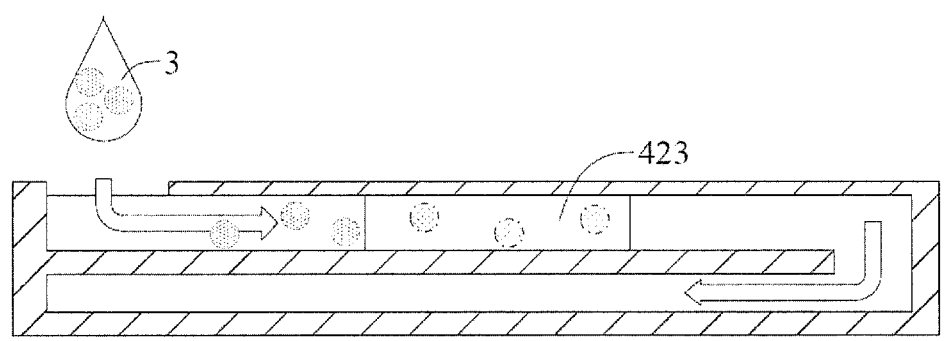

In an embodiment shown in FIG. 6(B), electroporation can be used in the lysis zone 423 for breaking membranes of cells, exosomes, or other vesicles.

Figure 6C:
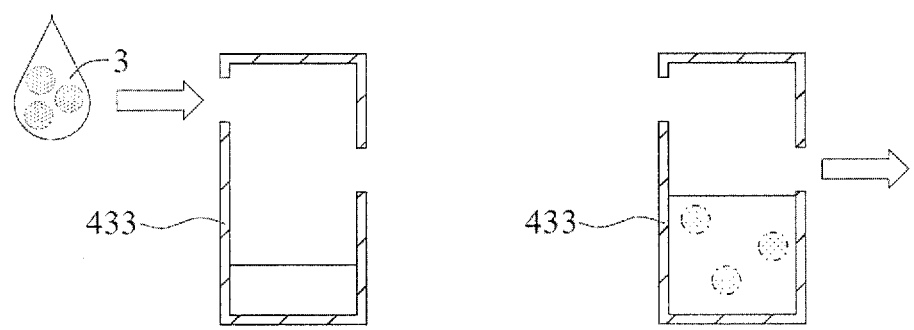
Figure 7A:
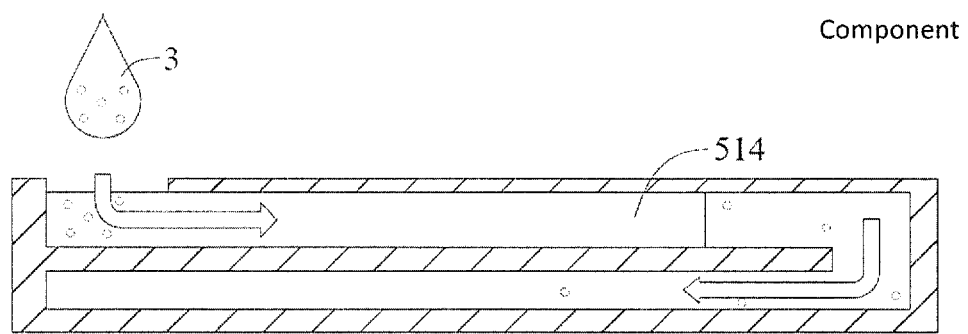
FIGS. 7(A)-(B) are cross-sectional views of dilution zones in different embodiments of the present disclosure.

In an embodiment shown in FIG. 6(C), the lysis zone 433 can be a lower tank containing lysis buffer for breaking membranes of cells, exosomes, or other vesicles. As illustrated, a biosample 3 flows into the lower tank and is sufficiently mixed with the lysis buffer. When the volume of the mixed solution (containing biosample 3 and the lysis buffer) exceeds a predetermined volume, the mixed solution flows out the lower tank and enters other zones.

d. Dilution Zone:

Dilution zone is designed for diluting concentrations of specific components for subsequent detections. In an embodiment shown in FIG. 7(A), the dilution zone 514 is designed to enable components in biosample 3 to have different flow rates, caused by differences in size, electrical property, specificity or affinity of the components. Thus, specific components in the channel can be diluted.

In another embodiment, a dilution zone can be featured with magnetohydrodynamics (MHD)-based flow control. For example, biomarkers in a biosample can form complexes with reporters in a mixing/reaction zone 322 (FIG. 5(B)) prior to entering the dilution zone 514 (FIG. 7(A)), herein the complexes and the unreacted reporters carry different net surface charges. While the complexes and the unreacted reporters flow through the dilution zone 514, they all experience an applied magnetic field perpendicular to the dilution zone 514. Consequently, flow velocity of the complexes and that of unreacted reporters are differentiated by different electromagnetic forces. In the same manner, a flow velocity of undesired components can be controlled to leave the dilution zone 514 faster. Hence, the undesired components are diluted in the dilution zone 514.

Figure 7B:
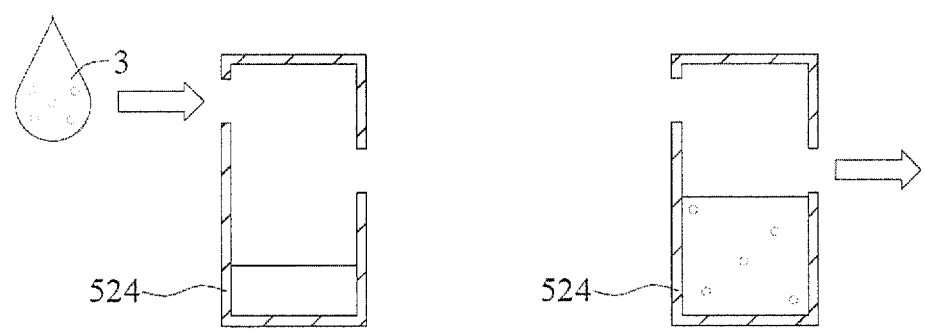

In another embodiment, the dilution zone 524 can be a lower tank containing a dilution buffer, as shown in FIG. 7(B). In this embodiment, a biosample 3 flows into the lower tank and is sufficiently mixed with the dilution buffer. When the volume of the mixed solution (containing the biosample 3 and the dilution buffer) exceeds a predetermined volume, the mixed solution will overflow the lower tank and enters other zones.

e. Concentration Zone:

Concentration zone is designed for increasing the concentration of target biomarkers to improve sensitivity of detection. In an embodiment shown in FIG. 8(A), a concentration zone 615 is designed to enable different components in a biosample 3 to have different flow rates caused by pore size, hydrophobicity or hydrophilicity of the concentration zone 615, and by electrical properties, specificities, or affinities of components. Therefore, a flow rate of target biomarkers is differentiated from that of other interfering substances. Consequently, target biomarkers can be concentrated at the concentration zone 615.

Figure 8A:
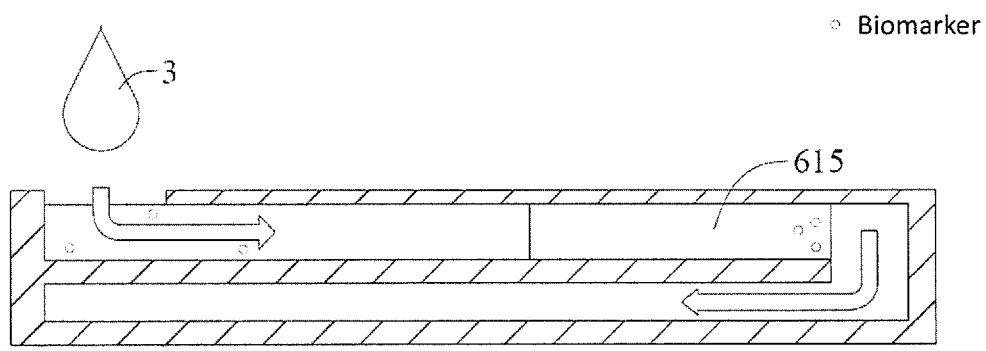
FIGS. 8(A)-(B) are cross-sectional views of concentration zones in different embodiments of the present disclosure.

In another embodiment, the concentration zone 615 (FIG. 8(A)) can be designed with the concept of magnetohydrodynamics (MHD). For instance, biomarkers mix with reporters in a mixing/reaction zone to form complexes prior to entering the concentration zone 615. Herein, the complexes and the unreacted reporters will carry different net surface charges. Subsequently, a given magnetic field, applied to both the complexes and the unreacted reporters with different net surface charges, causes a difference in flow velocities of the complexes and the unreacted reporters. Therefore, the complexes will be specifically driven toward the concentration zone 615.

Figure 8B:
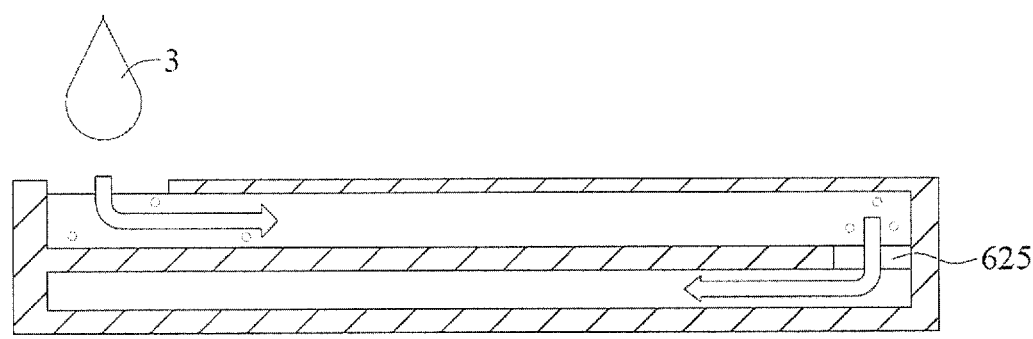

In another embodiment shown in FIG. 8(B), a concentration zone 625 can be a filter, so that target biomarkers are retained by the filter and is thus concentrated in front of the filter 625.

Figure 8C:
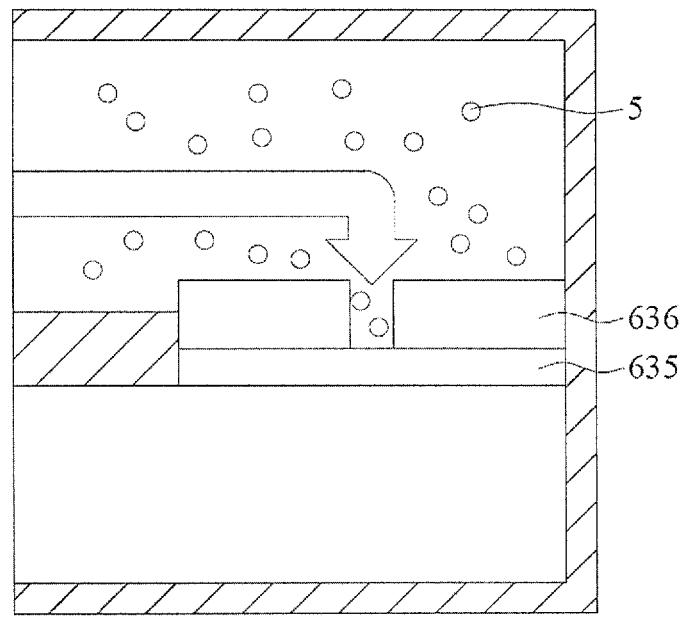
FIGS. 8(C)-(D) are cross-sectional views of concentration zones combined with detection zones in different embodiments of the present disclosure.
Figure 8D:
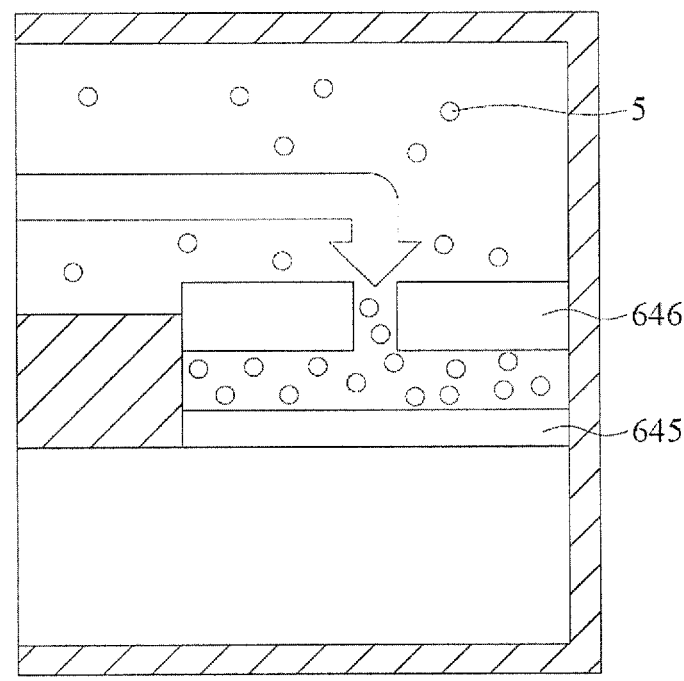
Figure 9A:
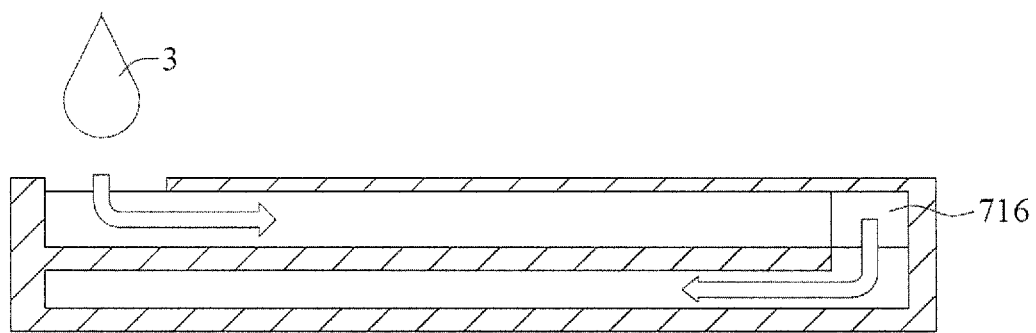
FIG. 9(A) is a cross-sectional view of a detection zone according to an embodiment of the present disclosure.

In an embodiment shown in FIG. 8(C) and FIG. 8(D), concentration zones 635 and 645 can be arranged in combination of detection zones 636 and 646, respectively. Specifically, the detection zones 636 and 646 can be arranged around the concentration zones 635 and 645 to improve sensitivity of subsequent detection. In an embodiment shown in FIG. 8(D), the concentration zone 645 and the detection zone 646 form a chamber to trap target biomarkers 5, so that the signal-to-noise ratio and the resultant sensitivity will be improved.

f. Detection Zone:

The detection zone (FIG. 9(A)) is designed for detecting target biomarkers in a biosample 3. A detection mechanism applied in the present disclosure can be selected from any applicable detection mechanisms in technical fields. For example, the detection can be performed by using an optical sensor (e.g., microscopy, infrared, Raman, magneto-optic Kerr effect (MOKE)), a magnetic sensor, a thermal sensor, an electrical counter, a radar, an ultrasound sensor, an electromagnetic radiation sensor, etc. The detection zone 716 can be integrated with any of the aforementioned functional zones to improve sensitivity and specificity. In an embodiment shown in FIG. 9(A), a detection zone 716 is provided at a corner of the channel. However, persons skilled in the art should understand that the detection zone 716 can be provided at any locations of the channel according to practical needs.

Figure 9B:
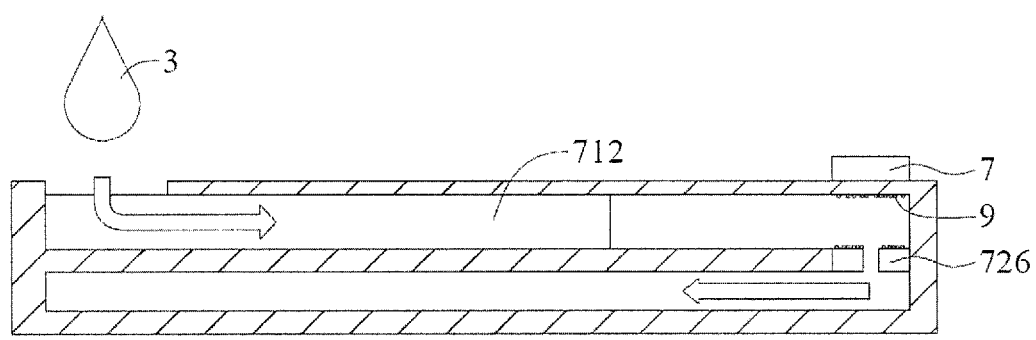
FIG. 9(B) is a cross-sectional view of a detection zone using magnetic particles as a reporter according to an embodiment of the present disclosure.

In an embodiment shown in FIG. 9(B), a magnet 7 is disposed adjacent to a detection zone 726 for increasing signal-to-noise ratio. When a biosample 3 passes through a mixing/reacting zone 712, target biomarkers in the biosample 3 are sufficiently mixed and react with reporters, i.e. magnetic particles 9. Afterwards, biomarker-magnetic-particle complexes and unreacted magnetic particles 9 flow through mixing/reaction zone 712 toward detection zone 726. Biomarker-magnetic-particle complexes will be conjugated by corresponding recognition elements on the detection zone 726. Noticeably, the conjugation between the complexes and the recognition elements is based on affinity between the biomarkers and the recognition elements. In the meanwhile, unconjugated magnetic particles 9 will be removed from the detection zone 726 by using the magnet 7 above.

Figure 9C:
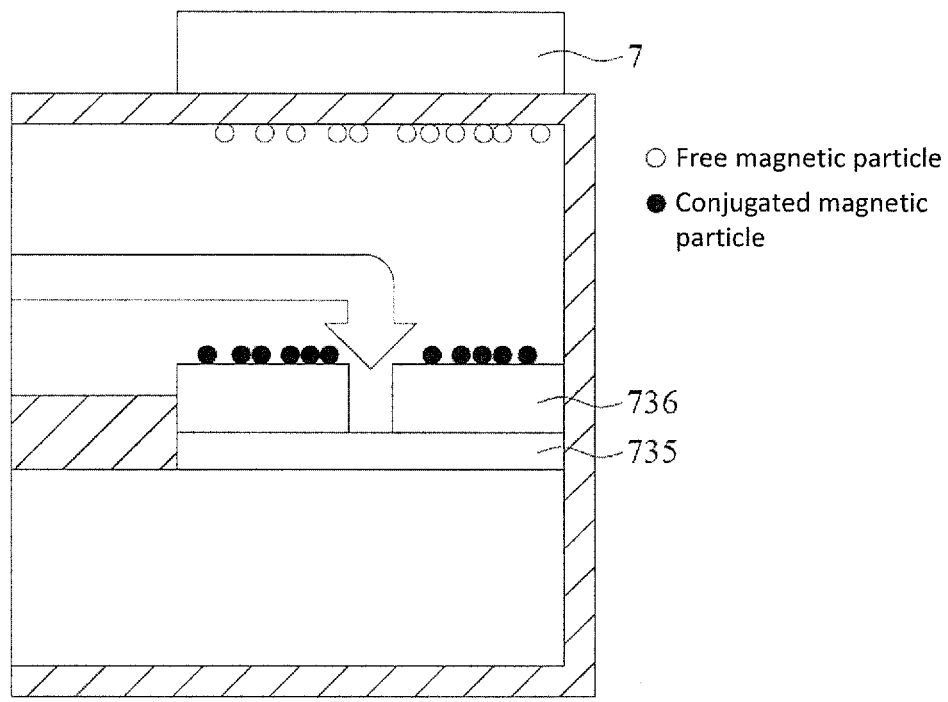
FIGS. 9(C)-(D) are cross-sectional views of detection zones combined with concentration zones using magnetic particles as a reporter in different embodiments of the present disclosure.
Figure 9D:
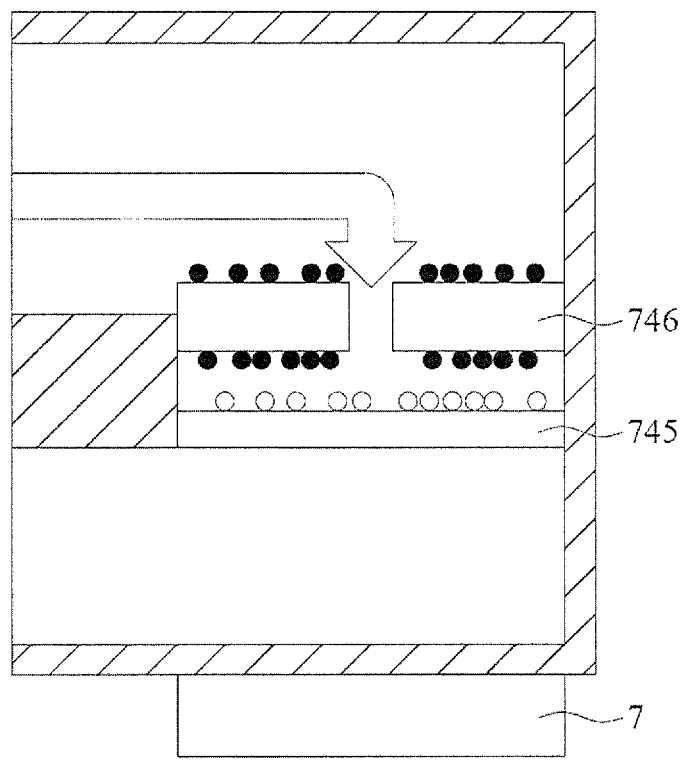

In addition, the aforementioned embodiment can be further modified (see FIG. 9(C) and FIG. 9(D)). For example, the detection zones 736 and 746 can be integrated with additional concentration zones 735 and 745, respectively, to improve the signal-to-noise ratio and the consequent sensitivity. It should be appreciated that the arrangement of the detection zone and the concentration zone is not limited thereto.

g. Absorbent Zone:

An absorbent zone 117 (FIG. 2) is designed based on the nature of surface tension to create a force to drive a flow of a biosample 3. Moreover, the absorbent zone can be used to assist a removal of interfering substances from the detection zone 116 (FIG. 2) by absorbing interfering substances therein.

The description above only shows embodiments for presenting exemplary functions and efficacy of the functional zones. It should be noted that the functional zones of the present disclosure is not limited to the functional zones mentioned above. Other functional zones can also be provided in the system of the present disclosure according to the practical needs.

In the following, a designated distribution is described in details.

Figure 10:
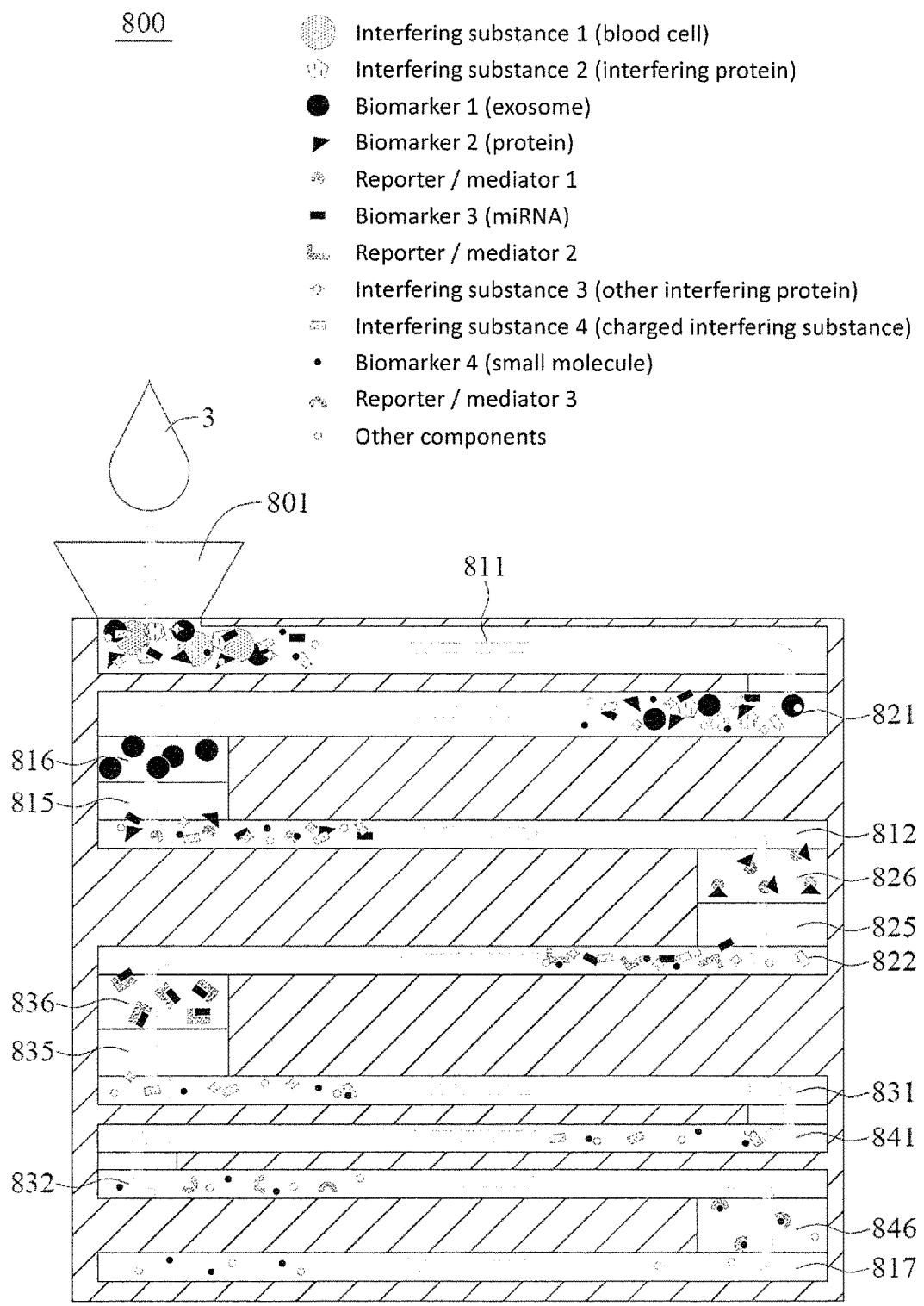
FIG. 10 shows a cross-sectional view of the microfluidic system according to an embodiment of the present disclosure.

In an embodiment shown in FIG. 10 (numbers in FIG. 10 are described in the reference sign list), several types of biomarkers are detected based on sizes. For example, exosomes, proteins, miRNAs, and small molecules are sequentially detected based on their sizes.

Figure 11:
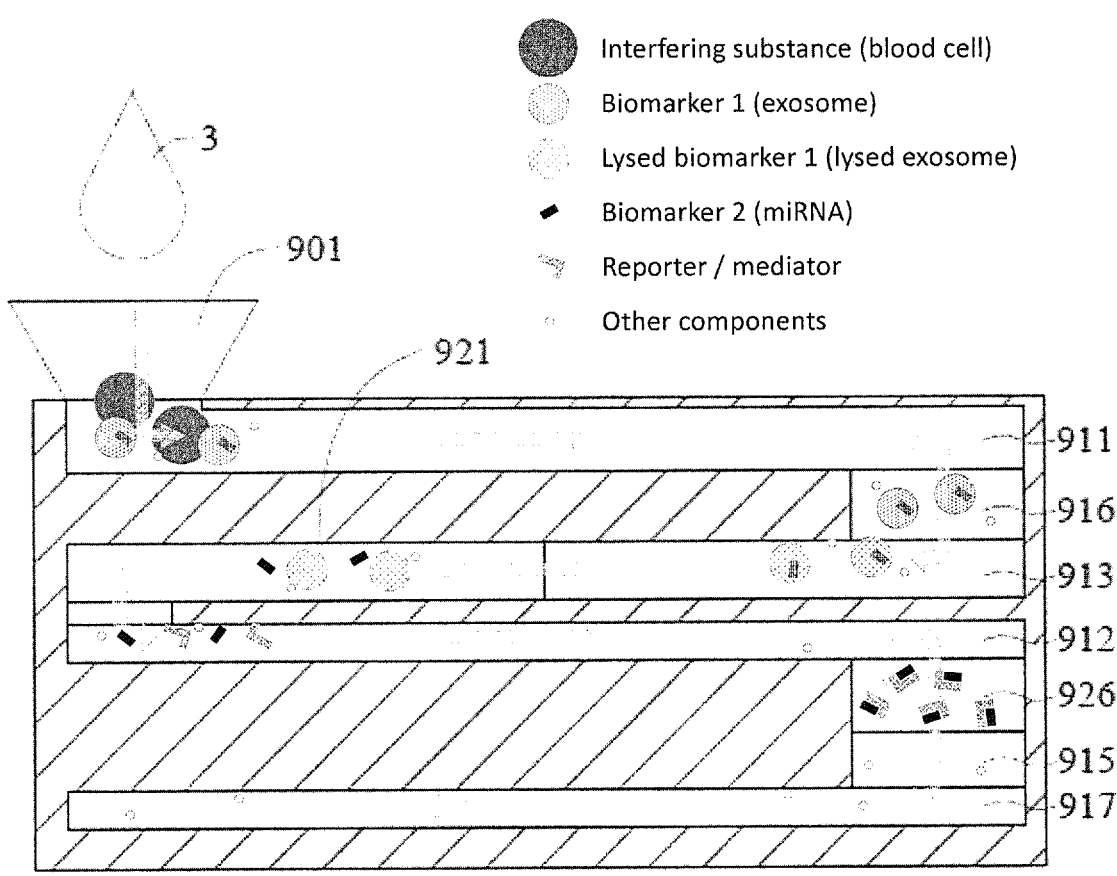
FIG. 11 shows a cross-sectional view of the microfluidic system according to another embodiment of the present disclosure.

In an embodiment shown in FIG. 11 (numbers in FIG. 11 are described in the reference sign list), a designated distribution is based on locations of target biomarkers. For instance, biomarkers outside a bio-particle will be firstly detected, then those inside the bio-particle will be detected subsequently. Another example is that, surface proteins of exosome are firstly detected, and then miRNA inside exosome are detected afterwards.

Figure 12:
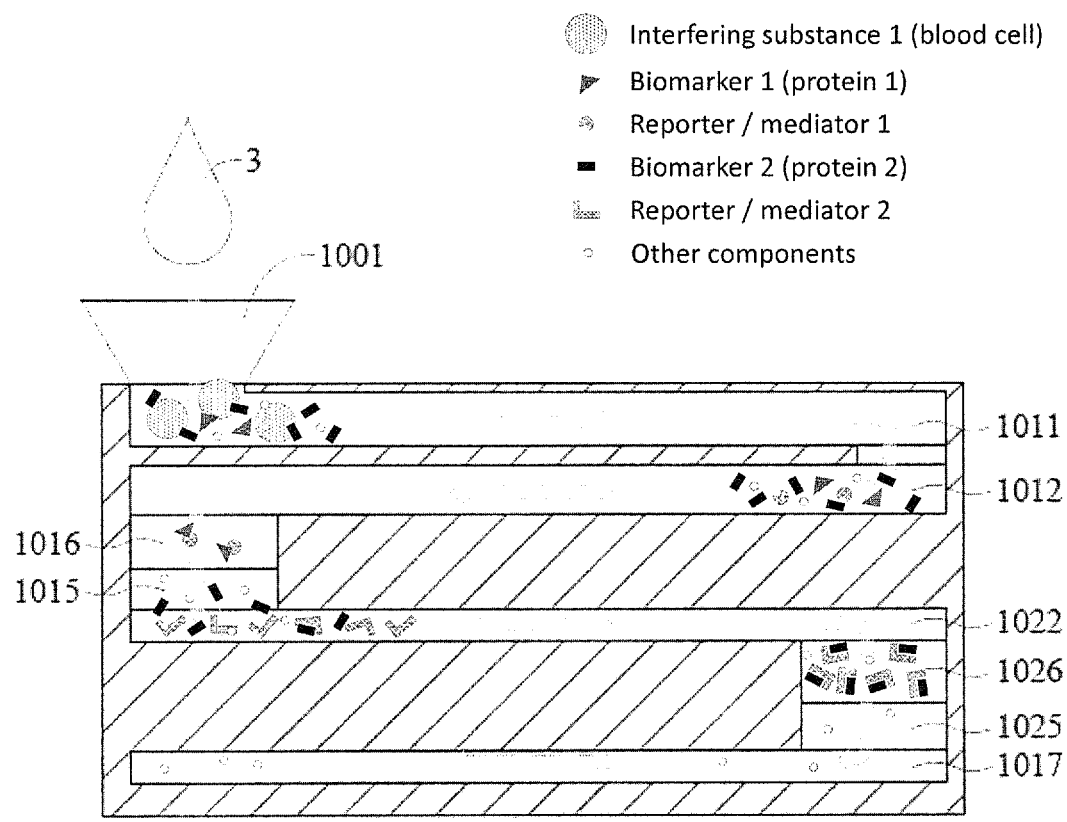
FIG. 12 shows a cross-sectional view of the microfluidic system according to another embodiment of the present disclosure.

In an embodiment shown in FIG. 12 (numbers in FIG. 12 are described in the reference sign list), a designated distribution can be based on concentrations of biomarkers. Namely, biomarkers in a low concentration will be detected early.

The exemplary system for detecting biomarkers of the present disclosure will now be described in details with reference to the drawings to show advantages and efficacy of the present disclosure. The disclosure, however, should not be construed as being limited to the specific embodiments set forth herein.

Embodiment 1

As shown in FIG. 10, a system 800 according to the embodiment is used to detect multiple biomarkers, including exosomes, proteins, miRNAs, and small molecules in a biosample 3. In an example, the biosample 3 is whole blood. The system 800 may be operated by following steps:

1. Injecting the biosample 3 into an inlet 801 of the system 800;
2. Enabling the biosample 3 to flow through a first filtration/separation zone 811 to obtain processed blood, such as plasma or serum, by filtering out undesired blood cells therein;
3. Enabling the processed blood to flow through a second filtration/separation zone 821 for removal of undesired proteins;
4. Enabling the biosample 3 to flow through a first detection zone 816 combined with a first concentration zone 815 to detect exosomes, wherein the first concentration zone 815 has appropriate porosity (about 30-150 nm);
5. Enabling the biosample 3 to flow through a first mixing/reaction zone 812 to sufficiently mix proteins therein with reporters;
6. Enabling the biosample 3 to flow through a second detection zone 826 combined with a second concentration zone 825 to detect the proteins, where the second concentration zone 825 has appropriate porosity;
7. Enabling the biosample 3 to flow through a second mixing/reaction zone 822 to sufficiently mix miRNAs therein with reporters;
8. Enabling the biosample 3 to flow through a third detection zone 836 combined with a third concentration zone 835 having appropriate porosity to detect the miRNAs;
9. Enabling the biosample 3 to flow through a third filtration/separation zone 831 to remove undesired proteins;
10. Enabling the biosample 3 to flow through a fourth filtration/separation zone 841 to remove undesired charged interfering substances;
11. Enabling the biosample 3 to flow through a third mixing/reaction zone 832 to sufficiently mix small molecules therein with reporters; and
12. Enabling the biosample 3 to flow through a fourth detection zone 846 to detect the small molecules.

In the embodiment, various zones are provided to perform different functions, while it should be appreciated that the present disclosure is not limited to the specific zones above. In fact, the arrangement of the zones can be adjusted upon actual needs. In the embodiment, a driving mechanism that enables the biosample 3 to flow along the channel is surface tension provided by an absorbent zone 817.

Embodiment 2

As shown in FIG. 11, a system 900 according to the embodiment is used to detect two kinds of biomarkers, including exosomes and miRNAs inside exosomes, in a biosample 3. In an example, the biosample 3 is whole blood. The system 900 may be operated by the following steps:

1. Injecting the biosample 3 into an inlet 901 of the system 900;
2. Enabling the biosample 3 to flow through a first filtration/separation zone 911 to obtain processed blood, such as plasma or serum, by filtering out undesired blood cells therein;
3. Enabling the processed blood to flow through a first detection zone 916 to detect exosomes;
4. Enabling the biosample 3 to flow through a first lysis zone 913 to break the exosomes and to release miRNAs from the exosomes therein;

5. Enabling the biosample 3 to flow through a second filtration/separation zone 921 for the removal of lysed exosomes;
6. Enabling the biosample 3 to flow through a first mixing/reaction zone 912 to sufficiently mix the miRNAs therein with reporters; and
7. Enabling the biosample 3 to flow through a second detection zone 926 combined with a first concentration zone 915 having appropriate porosity to detect the miRNAs.

In the embodiment, various zones are provided to perform different functions, while it should be appreciated that the present disclosure is not limited to the specific zones above. In fact, the arrangement of the zones can be adjusted upon actual needs. In the embodiment, a driving mechanism that enables the biosample 3 to flow along the channel is surface tension provided by an absorbent zone 917.

Embodiment 3

As shown in FIG. 12, a system 1000 according to the embodiment is used to detect two biomarkers, one of them (biomarker 1) is in a small amount, in a biosample 3. In an example, the biosample 3 is whole blood. The system 1000 may be operated by the following steps:
1. Injecting the biosample 3 into an inlet 1001 of the system 1000;
2. Enabling the biosample 3 to flow through a first filtration/separation zone 1011 to obtain processed blood, such as plasma or serum, by filtering out undesired blood cells therein;
3. Enabling the processed blood to flow through a first mixing/reaction zone 1012 to sufficiently mix proteins 1 therein with reporters;
4. Enabling the biosample 3 to flow through a first detection zone 1016 combined with a first concentration zone 1015 having appropriate porosity to detect the proteins 1;
5. Enabling the biosample 3 to flow through a second mixing/reaction zone 1022 to sufficiently mix proteins 2 therein with reporters; and
6. Enabling the biosample 3 to flow through a second detection zone 1026 combined with a second concentration zone 1025 having appropriate porosity to detect the proteins 2.

In the embodiment, various zones are provided to perform different functions, while it should be appreciated that the present disclosure is not limited to the specific zones above. In fact, the arrangement of the zones can be adjusted upon actual needs. In the embodiment, a driving mechanism that enables the biosample 3 to flow along the channel is surface tension provided by an absorbent zone 1017.

Embodiment 4

Figure 13:
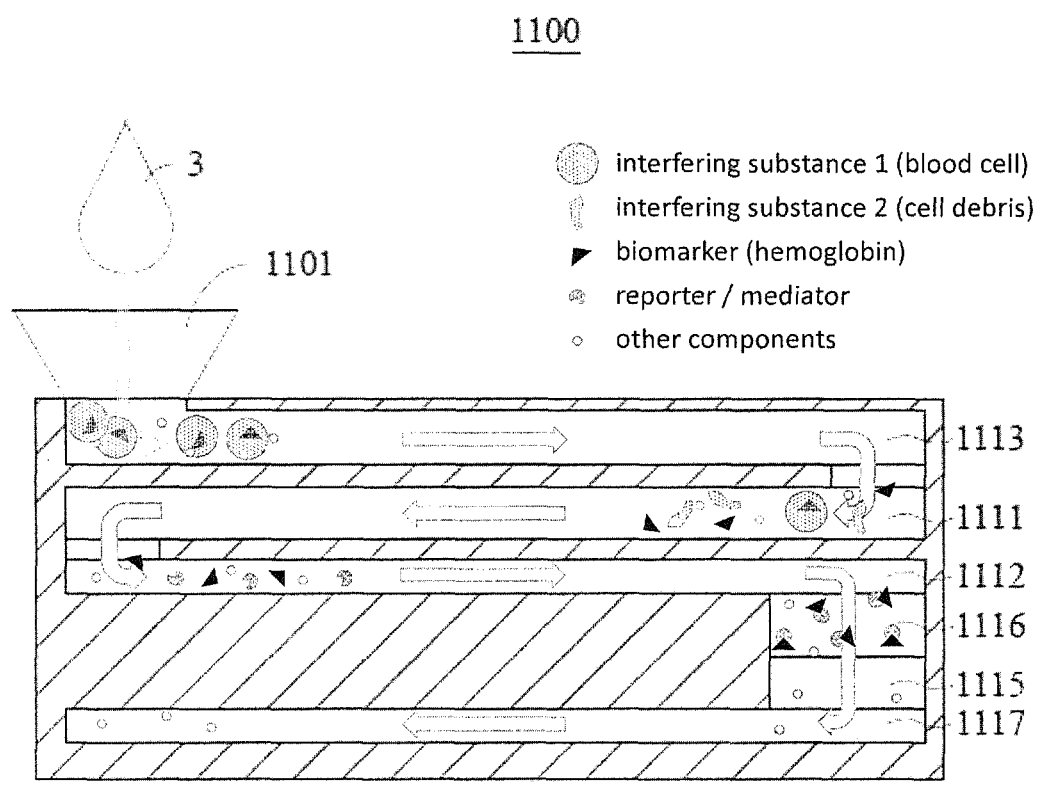
FIG. 13 shows a cross-sectional view of the microfluidic system according to another embodiment of the present disclosure.

As shown in FIG. 13, a system 1100 according to the embodiment is used to detect hemoglobin in a biosample 3. In an example, the biosample 3 is whole blood. The system 1100 may be operated by following steps:
1. Injecting the biosample 3 into an inlet 1101 of the system 1100;
2. Enabling the biosample 3 to flow through a first lysis zone 1113 to break blood cells therein;
3. Enabling the biosample 3 to flow through a first filtration/separation zone 1111 to filter out interfering substances, undesired cell debris and blood cells that are not broken;
4. Enabling the biosample 3 to flow through a first mixing/reaction zone 1112 to sufficiently mix hemoglobin therein with mediators; and
5. Enabling the biosample 3 to flow through a first detection zone 1116 combined with a first concentration zone 1115 to detect the hemoglobin, where the first concentration zone 1115 has appropriate porosity.

In the embodiment, various zones are provided to perform different functions, it should be appreciated that the present disclosure is not limited to the specific zones above, and the arrangement of the zones can be adjusted upon actual needs. In the embodiment, the driving mechanism that enables the biosample 3 to flow along the channel is surface tension provided by an absorbent zone 1117.

Embodiment 5

As shown in FIG. 3(B), a system according to the embodiment is used to count an amount of cells in a biosample 3. In an example, the biosample 3 is whole blood. The system may be operated by following steps:
1. Injecting the biosample 3 into an inlet 201 of the system;
2. Dividing the biosample 3 into channels 203 and 205, wherein the channel 205 is a cell counting channel having a detection zone 216 for counting cells according to an optical, electrical, or magnetic sensing signals; and
3. Enabling the biosample 3 to flow through the detection zone 216 in the cell counting channel 205 for cell counting.

In the embodiment, various zones are provided to perform different functions, it should be appreciated that the present disclosure is not limited to the specific zones above, and the arrangement of the zones can be adjusted upon actual needs. In the embodiment, a driving mechanism that enables the biosample 3 to flow along the channels 203, 205 may be surface tension or other applicable driving mechanisms.

The present disclosure has been described using exemplary embodiments to illustrate the principles and the effects of the present disclosure, but not intend to limit the present disclosure. The present disclosure without departing from the spirit and scope of the premise can make various changes and modifications by a person skilled in the art. Therefore, the scope of the disclosure should be defined by appended claims.

What is claimed is:
1. A method of detecting multiple biomarkers, comprising:
providing an inlet region for receiving a sample;
providing a driving mechanism to force the sample to move along a channel;
providing the channel for allowing the sample to move along thereof, wherein the channel is a continuous winding path with bending corners;
distributing at least three functional zones along the channel, configured to retain biomarkers based on the biomarkers' sizes, wherein a size of a biomarker retained in a first functional zone is larger than that in a second functional zone, and the size of the biomarker retained in the second functional zone is larger than that in a third functional zone, wherein each of the functional zones comprises a filtration/separation zone, a detection zone, and a concentration zone, wherein the detection zone is provided at one of the bending corners and the concentration zone is integrated with the detection zone; and detecting the biomarker at each of the functional zones.

2. The method of claim 1, wherein the at least three functional zones are arranged based on a condition comprising at least one selected from the group consisting of a location of a biomarker, a concentration of a biomarker, a biometric of a biomarker, and a combination thereof.

3. The method of claim 1, wherein the driving mechanism is provided by a surface tension or a capillarity action.

4. The method of claim 1, wherein the channel comprises discrete compartments, wherein each compartment contains at least one functional zone.

5. The method of claim 1, wherein the at least three functional zones further comprise at least one of a mixing/reaction zone, a lysis zone, a dilution zone, an absorbent zone, and a combination thereof.

6. The method of claim 5, wherein the lysis zone comprises at least one condition selected from the group consisting of lysing cells, exosomes, or other vesicles in the sample by a lysing agent; lysing cells, exosomes, or other vesicles in the sample by electroporation; lysing cells, exosomes, or other vesicles in the sample in a lower tank containing a lysis buffer for mixing with the sample; and a combination thereof.

7. The method of claim 5, wherein the dilution zone comprises at least one condition selected from the group consisting of diluting specific components in the sample by causing different flow rates of specific components; diluting specific components in the sample by using a magnetohydrodynamics (MHD)-based flow control; diluting specific components in the sample by using a lower tank containing a dilution buffer for mixing with the sample; and a combination thereof.

8. The method of claim 1, wherein the channel has different cross-sectional areas corresponding to different functional zones for accelerating or decelerating the movement of the sample.

9. The method of claim 1, wherein the channel is formed by different materials or treated by a surfactant agent, an ionized plasma, or a wax for accelerating or decelerating the movement of the sample.

10. The method of claim 1, further comprising a magnetohydrodynamics (MHD)-based flow control for accelerating or decelerating the movement of the sample.

11. The method of claim 1, wherein the filtration/separation zone comprises at least one condition selected from the group consisting of retaining one or more components in the sample with respect to a pore size of a filter or a dimension of a micro-channel; separating one or more components in the sample according to electrical properties, specificities or affinities of the components; separating one or more components in the sample by using a magnetohydrodynamics (MHD)-based flow control; and a combination thereof.

12. The method of claim 1, further comprising a magnet adjacent to the detection zone for separating unreacted magnetic particles from reacted magnetic particles.

13. The method of claim 1, wherein the sample comprises at least one biomarker selected from the group consisting of cells, exosomes, proteins, DNAs, RNAs, miRNAs, small molecules, metabolites, antibodies, nucleic acids, enzymes, and a combination thereof.

14. The method of claim 1, wherein the concentration zone comprises at least one condition selected from the group consisting of using pore sizes, hydrophobicity or hydrophilicity of the channel; electrical properties, specificities or affinities of the components in the sample to control a flow rate of components; concentrating components in the sample by using a magnetohydrodynamics (MHD)-based flow control; retaining components in the sample with respect to the pore size of a filter; and a combination thereof.

15. A system for detecting multiple biomarkers, comprising:
an inlet region for receiving a sample;
a driving mechanism to force the sample to move along a channel;
the channel connected with the inlet region, the channel having a continuous winding path with bending corners, wherein the channel allows the sample to move along thereof;
multiple functional zones arranged along the channel in a designated distribution, the multiple functional zones configured to retain biomarkers based on the biomarkers' sizes, wherein a size of a biomarker retained in a first functional zone is larger than that in a second functional zone, and the size of the biomarker retained in the second functional zone is larger than that in a third functional zone, wherein each of the functional zones comprises a filtration/separation zone, a detection zone, and a concentration zone, wherein the detection zone is provided at one of the bending corners and the concentration zone is integrated with the detection zone; and
detectors for detecting the biomarker at each of the functional zones.

16. The system of claim 15, wherein the designated distribution is arranged based on the condition comprising at least one selected from the group consisting of a location of a biomarker, a size of a biomarker, a concentration of a biomarker, a biometric of a biomarker, and a combination thereof.

17. The system of claim 15, wherein the sample moves along by surface tension or capillarity action.

18. The system of claim 15, wherein the channel comprises discrete compartments, wherein each compartment contains at least one functional zone.

19. The system of claim 15, wherein the functional zones further comprises at least one selected from the group consisting of a mixing/reaction zone, a lysis zone, a dilution zone, a concentration zone, a detection zone, an absorbent zone, and a combination thereof.

20. The system of claim 19, wherein the filtration/separation zones independently comprises at least one condition selected from the group consisting of retaining one or more components in the sample with respect to the pore size of a filter or the dimension of a micro-channel; separating one or more components in the sample according to electrical properties, specificities, or affinities of the components; separating one or more components in the sample by using magnetohydrodynamics (MHD)-based flow control; and a combination thereof.

21. The system of claim 19, wherein the lysis zone comprises at least one condition selected from the group consisting of lysing cells, exosomes, or other vesicles in the sample by a lysing agent; lysing cells, exosomes, or other vesicles in the sample by electroporation; lysing cells, exosomes, or other vesicles in the sample in a lower tank containing a lysis buffer for mixing with the sample; and a combination thereof.

22. The system of claim 19, wherein the dilution zone comprises at least one condition selected from the group consisting of diluting specific components in the sample by causing different flow rates of specific components; diluting specific components in the sample by using magnetohydrodynamics (MHD)-based flow control; diluting specific components in the sample by using a lower tank containing a dilution buffer for mixing with the sample; and a combination thereof.

23. The system of claim 19 further comprising a magnet adjacent to the detection zone for separating unreacted magnetic particles from reacted magnetic particles.

24. The system of claim 19, wherein the concentration zones independently comprise at least one condition selected from the group consisting of using pore sizes, hydrophobicity or hydrophilicity of the channel; electrical properties, specificities or affinities of components in the sample to control the flow rate of components; concentrating components in the sample by using magnetohydrodynamics (MHD)-based flow control; retaining components in the sample with respect to the pore size of a filter; and a combination thereof.

25. The system of claim 15, wherein the channel has different cross-sectional areas corresponding to different functional zones for accelerating or decelerating the movement of the sample.

26. The system of claim 15, wherein the channel is formed by different materials or treated by surfactant agent, ionized plasma, or wax for accelerating or decelerating the movement of the sample.

27. The system of claim 15, further comprising magnetohydrodynamics (MHD)-based flow control for accelerating or decelerating the movement of the sample.

28. The system of claim 15, wherein the sample comprises at least one biomarker selected from the group consisting of cells, exosomes, proteins, DNAs, RNAs, miRNAs, small molecules, metabolites, antibodies, nucleic acids, enzymes, and a combination thereof.

* * * * *